United States Patent [19]

Jansen et al.

[11] Patent Number: 5,634,566
[45] Date of Patent: Jun. 3, 1997

[54] COVER FOR A WASTE CONTAINER

[75] Inventors: Cornelis J. Jansen, Rijen; Stephanus F. Schilthuizen, Berkel-Enschot, both of Netherlands

[73] Assignee: Wiva Verpakkingen B.V., Netherlands

[21] Appl. No.: 284,587

[22] PCT Filed: Dec. 10, 1993

[86] PCT No.: PCT/EP93/03554

§ 371 Date: Aug. 10, 1994

§ 102(e) Date: Aug. 10, 1994

[87] PCT Pub. No.: WO94/13562

PCT Pub. Date: Jun. 23, 1994

[30] Foreign Application Priority Data

Dec. 11, 1992 [NL] Netherlands ............................ 9202150
Sep. 2, 1993 [NL] Netherlands ............................ 9301521

[51] Int. Cl.$^6$ ............................ B65D 51/18; B65F 1/16
[52] U.S. Cl. ............................ 220/254; 220/908; 220/293; 220/298; 220/303
[58] Field of Search ............................ 220/908, 293, 220/296, 298, 299, 300, 301, 302, 254, 366.1, 303; 215/332, 330, 318

[56] References Cited

U.S. PATENT DOCUMENTS

| | | | |
|---|---|---|---|
| 1,158,073 | 10/1915 | Payne | 220/293 X |
| 1,598,870 | 9/1926 | Merry | 220/293 |
| 1,907,254 | 5/1933 | Dodge | 215/330 |
| 1,975,498 | 10/1934 | Billerman | 220/300 X |
| 1,988,383 | 1/1935 | Hermani | |
| 2,627,359 | 2/1953 | Woodward | 220/293 X |
| 2,660,315 | 11/1953 | Lasky | 220/293 X |
| 2,661,862 | 12/1953 | Howe | 220/296 |
| 2,665,028 | 1/1954 | Hintz | 220/300 |
| 2,679,878 | 6/1954 | Stine | 220/300 |
| 2,797,016 | 6/1957 | Schwendler et al. | 220/300 |
| 2,953,277 | 9/1960 | Weltman | |
| 3,069,040 | 12/1962 | Corsette | 215/318 |
| 3,931,891 | 1/1976 | Peppler | 220/298 X |
| 4,190,170 | 2/1980 | Boyd | 220/366.1 |
| 4,245,753 | 1/1981 | Ellis | 220/296 X |
| 4,379,574 | 4/1983 | Leichtl | 220/300 X |
| 4,723,686 | 2/1988 | Pennisi | 220/300 |
| 5,150,803 | 9/1992 | Cartellone | 220/731 X |

FOREIGN PATENT DOCUMENTS

| | | | |
|---|---|---|---|
| 144886 | 8/1949 | Australia | 220/293 |
| 475573 | 7/1951 | Canada | 215/332 |
| 455172A2 | 4/1991 | European Pat. Off. | |
| 8912223 | 5/1990 | Germany | |
| 205540 | 1/1959 | Sweden | 220/296 |
| 679770 | 4/1992 | Switzerland | |
| 261370 | 4/1927 | United Kingdom | 220/296 |
| 2035972 | 6/1980 | United Kingdom | |
| 2226545 | 7/1990 | United Kingdom | |

*Primary Examiner*—Allan N. Shoap
*Assistant Examiner*—Nathan Newhouse
*Attorney, Agent, or Firm*—Webb Ziesenheim Bruening Logsdon Orkin & Hanson, P.C.

[57] ABSTRACT

Cover for a waste container consisting of a cover plate (3) with peripheral wall which fits onto the standing upper rim (2) of the container, in which cover plate is recessed a circular opening (4) which is closable by a circular lid (7), wherein an outer peripheral wall of the lid and the inner periphery of the recess have co-acting cams for locking the lid in the recess, wherein the cams (23, 24, 60, 62) are disposed in different levels or are elongate and are disposed sloping relative to the line of symmetry of the lid such that an opening is formed between the one end of a cam and the other end of the adjacent cam, which opening serves for passage of the co-acting cam, wherein the axially oriented lower surface of the one cam in addition to the opposite axial surface of the other co-acting cam have indentations for defining different closing positions of the lid in the cover plate, whereby one or more intermediate positions of the lid in which the lid can be removed, and an end position in which the lid is permanently locked are obtained.

15 Claims, 11 Drawing Sheets

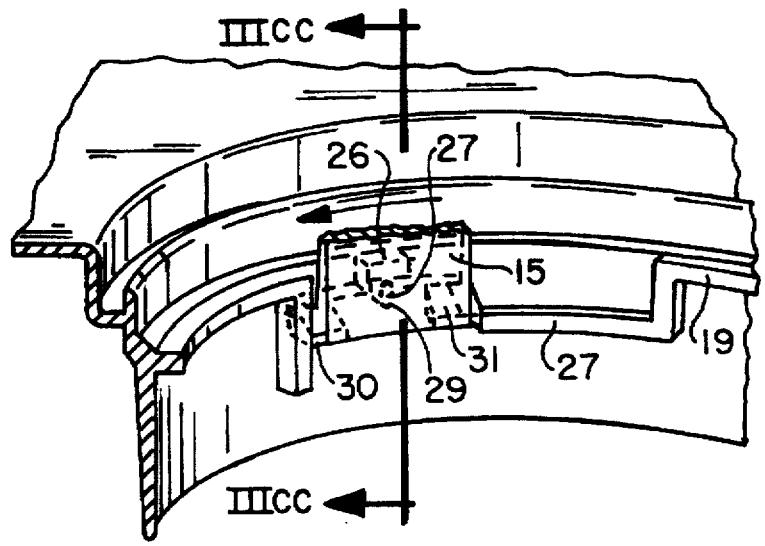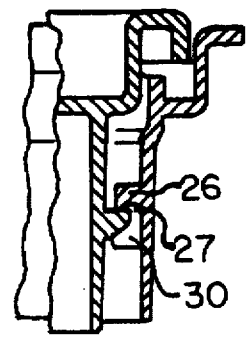
FIG. 3c
FIG. 3cc
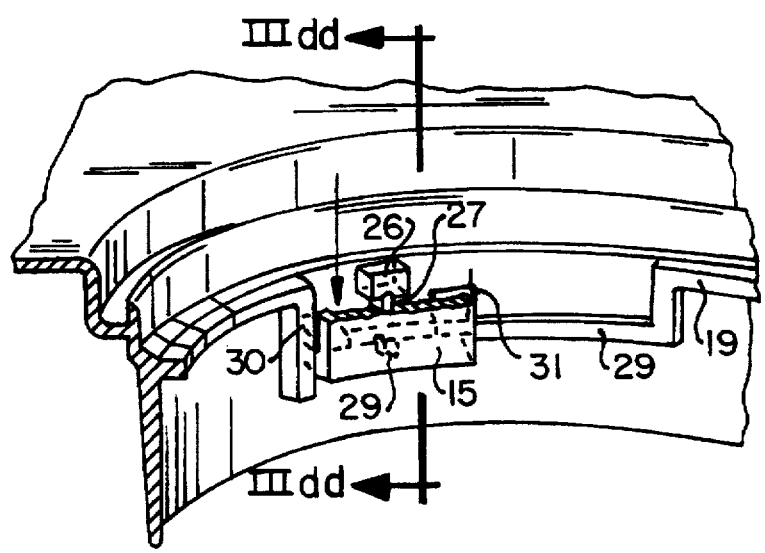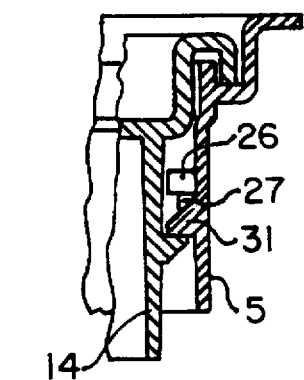
FIG. 3d
FIG. 3dd

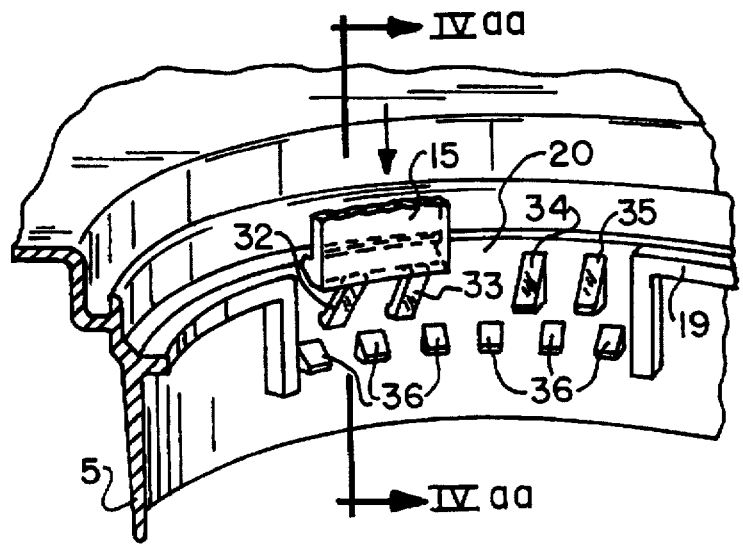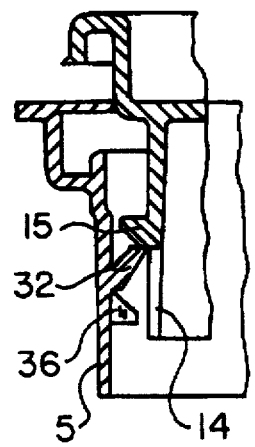
FIG. 4a
FIG. 4aa
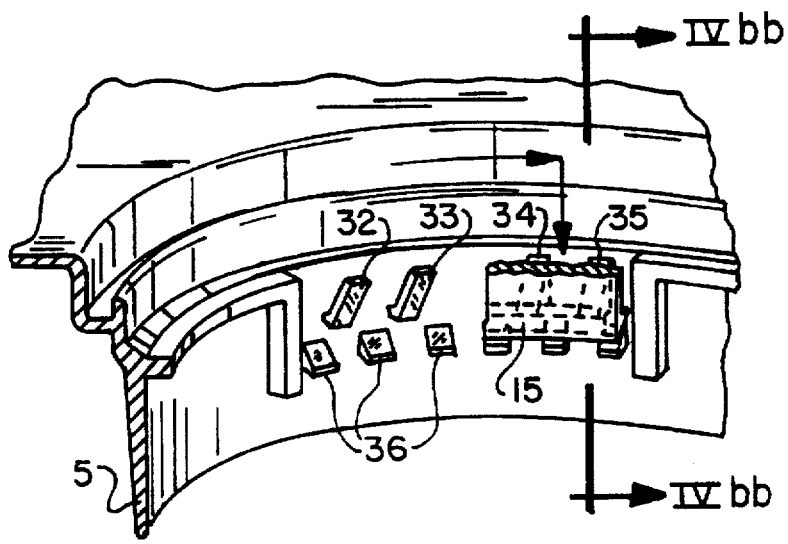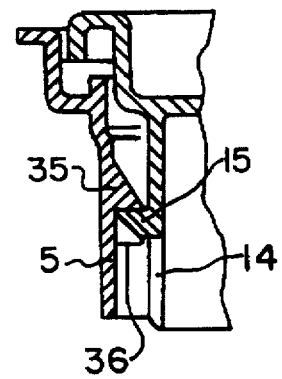
FIG. 4b
FIG. 4bb

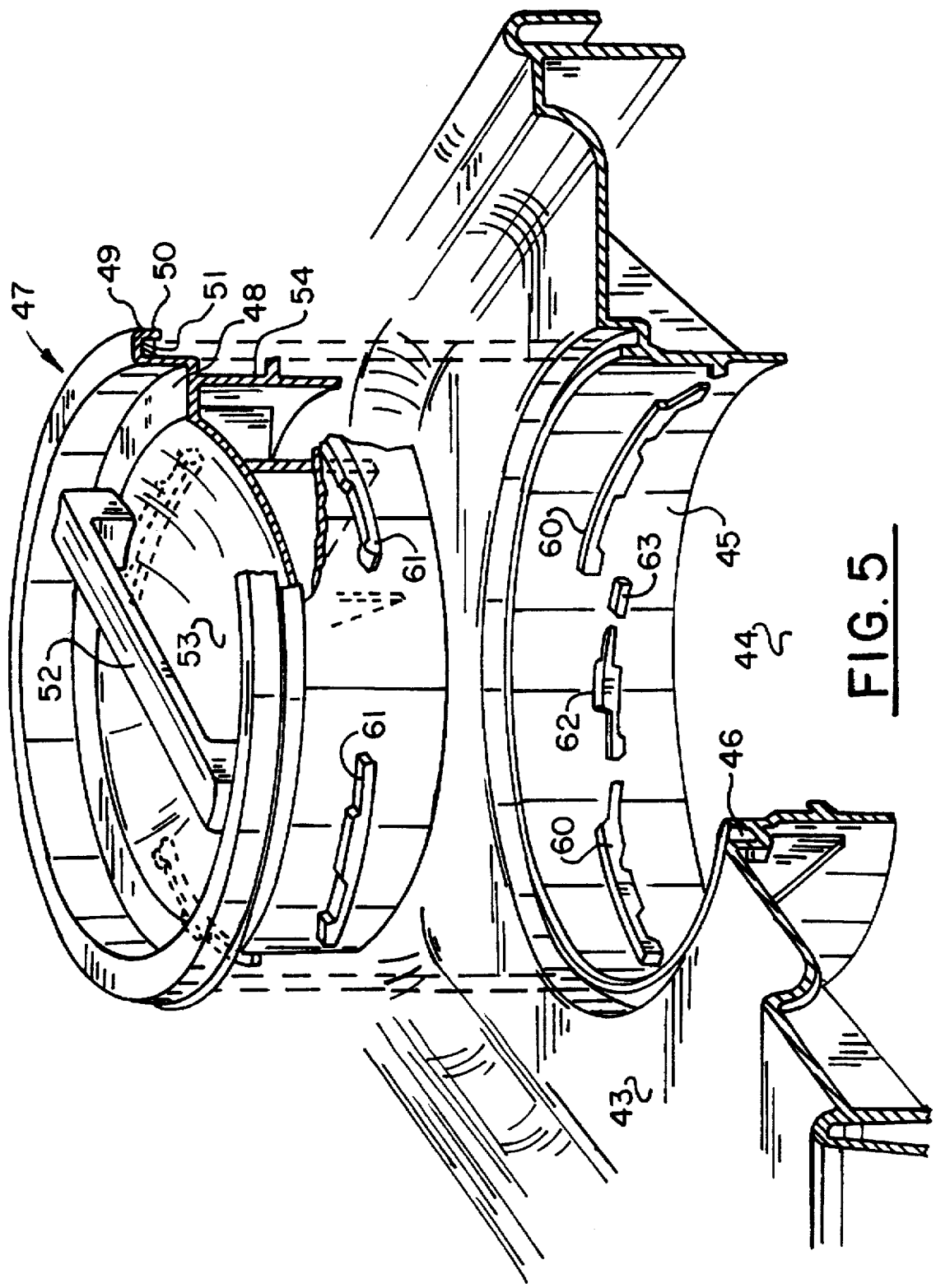

COVER FOR A WASTE CONTAINER

BACKGROUND OF THE INVENTION

1. Field of the Invention

The invention relates to a cover for a waste container consisting of a cover plate with peripheral wall which fits onto the standing upper rim of the container, in which cover plate is recessed a circular opening which is closable by a circular lid, wherein an outer peripheral wall of the lid and the inner periphery of the recess have co-acting cams for locking the lid in the recess.

2. Prior Art

The waste containers as referred to above are normally used for receiving waste for burning because of the infectious nature thereof. This is usually hospital waste, and such a container is filled up gradually. For this purpose the cover for the container can be placed in two positions, that is, a temporary position in which the cover can be lifted from the container in order to fill the container, as well as a permanent position wherein the cover is fixed permanently on the container which when filled is placed in an incinerator. The cover is moreover embodied with an additional opening which can be closed and which serves for admitting small amounts of waste and for monitoring the contents. In this case the entire cover does not have to be lifted. The present invention relates particularly to this small closable opening.

It is customary to give this opening a circular form and close it by means of a circular lid. This lid also has to be placed in different positions, in particular a temporary one in which the lid part can easily be detached again, wherein the additional requirement is made that the lid part serves as hand-grip to enable lifting of the wholly or partially filled container and moving thereof into a definitive closing position.

Heretofore it has been difficult to embody the closure of the lid part in the circular hole of a cover such that it suffices for the temporary and permanent closure and the carrying function thereof.

The invention has for its object to improve the closure of the lid part in the cover such that the above stated drawbacks are obviated.

SUMMARY OF THE INVENTION

The cover according to a first embodiment of the invention is distinguished in that the cams on the lid are formed like flexible hooks, cooperating with a plurality of co-acting cams on the cover, said co-acting cams are arranged in rows on different levels.

The cover according to a second embodiment is distinguished in that the cams are elongate and are disposed sloping relative to the line of symmetry of the lid such that an opening is formed between the one end of a cam and the other end of the adjacent cam, which opening serves for passage of the co-acting cam, wherein the axially oriented lower surface of the one cam in addition to the opposite axial surface of the other co-acting cam have indentations for defining different closing positions of the lid in the cover plate.

Due to the slopingly disposed cams the lid can be fixed temporarily to the cover through a small rotation relative thereto. The indentations prevent a counter-rotation of the lid in relation to the cover when the lid is lifted, whereby the cover could unexpectedly come loose of the lid part and waste possibly spill out of the container. A further rotation of the lid part will effect a more permanent closure.

In a further development of the cover according to the invention the other end of the co-acting cam is embodied in a hook form and co-acts with a resilient counter-member of the one cam so that a permanent hooking of the cams into one another is brought about when the lid part is rotated further, whereby a permanent closure results.

BRIEF DESCRIPTION OF THE DRAWINGS

Above mentioned and other features will be further elucidated in the figure description hereinbelow of two embodiments. In the drawing:

FIGS. 2aa–2ee show cross sectional views corresponding with FIGS. 2a–2e;

FIGS. 3a–3d show partly broken away detail views of a second embodiment of the invention;

FIGS. 3aa–3dd show cross sectional views corresponding with FIGS. 3a–3d;

FIGS. 4a–4d show detail views of the third embodiment depicted in FIG. 4;

FIGS. 4aa–4dd show cross sectional views corresponding with FIGS. 4a–4d;

FIG. 5 shows a detail on enlarged scale of the opening with lid part provided with closing cams according to a second embodiment of the invention;

DESCRIPTION OF THE PREFERRED EMBODIMENTS

Figure 1:
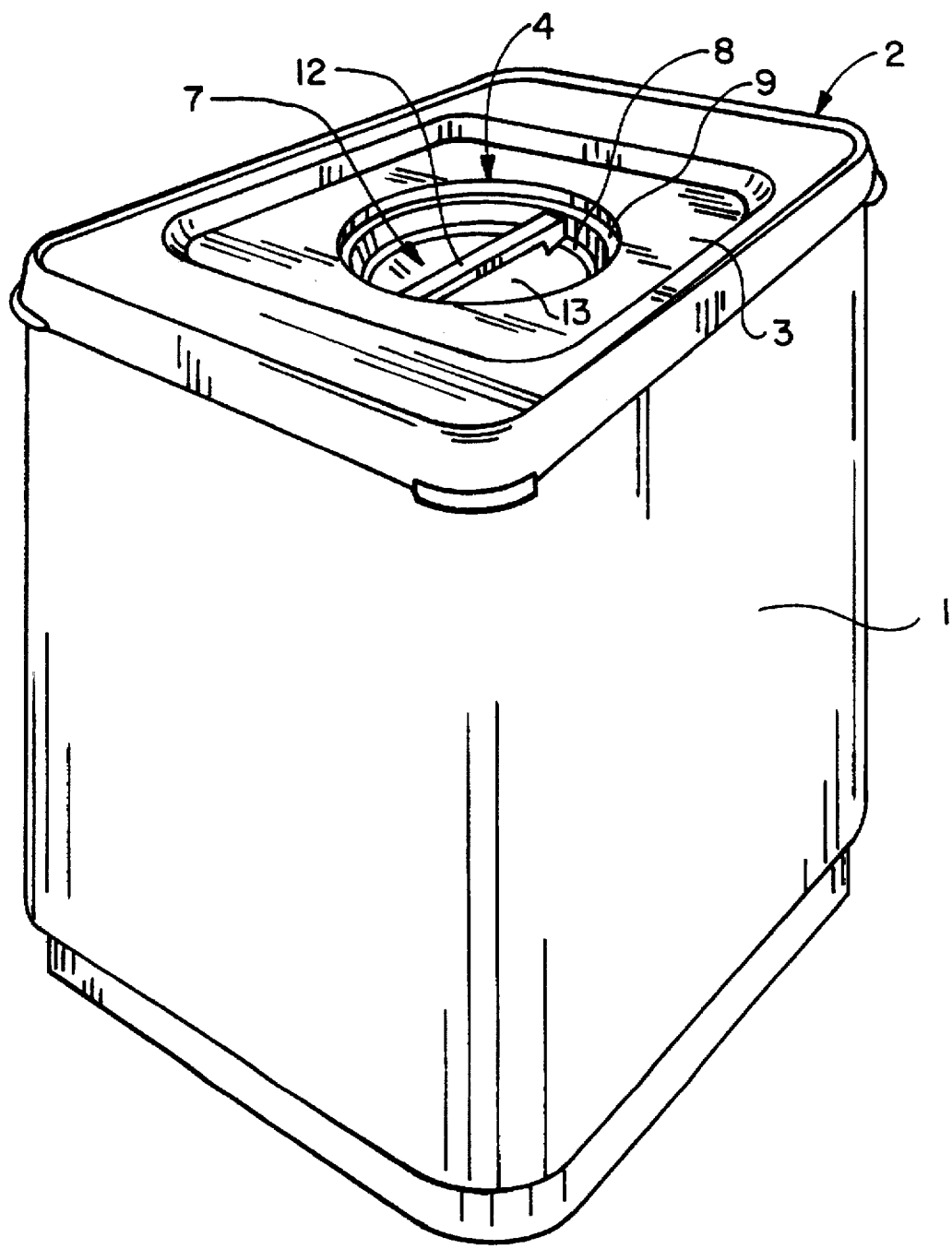
FIG. 1 shows a perspective view of a container provided with a cover according to the present invention.

Shown in FIGS. 1 is a container 1 which can have a random form and which can furthermore be manufactured of random material provided it can be incinerated harmlessly. Such a container is normally formed by means of injection or blow moulding.

The container i is open at its top and is closed by a cover 2. The manner of fastening the cover 2 onto the container i falls outside the scope of the invention and can take place in different ways, whether or not in a permanent state.

Figure 2A:
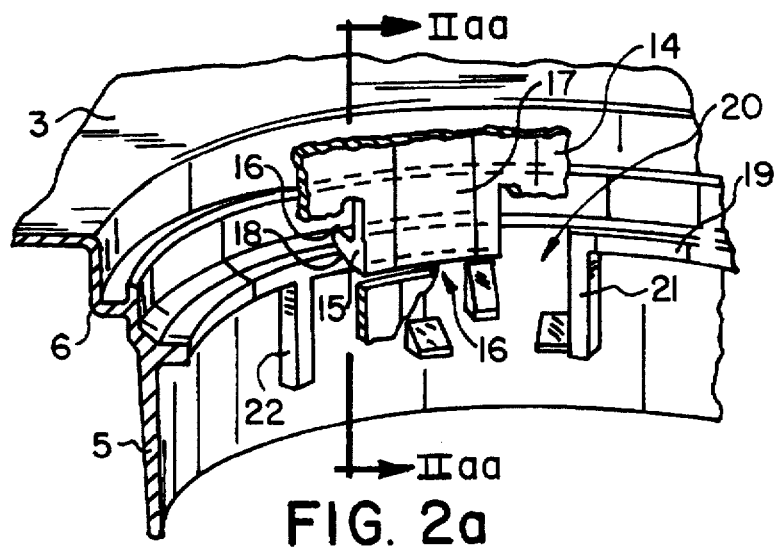
FIGS. 2a–2e show partly broken away detail views of a cover with a lid which is provided with cams according to a first embodiment of the invention.
Figure 2A:
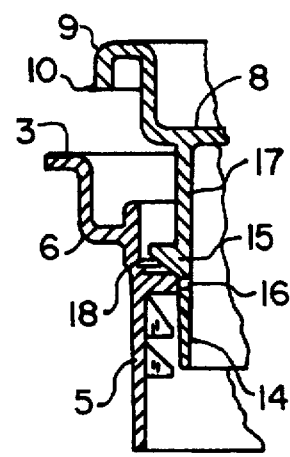

Cover 2 comprises a cover plate 3 in which is recessed an opening 4. As can be seen in FIG. 2a, the opening 4 is provided on the top with a downward extending skirting 5 defining an inner periphery which transposes into the cover plate 3 via a U-shaped edge portion 6.

Into the opening 4 can be placed a lid 7 which is formed substantially by a round plate 8 which is provided with an upward extending U-shaped edge 9 with a downward facing outer flange 10. Flange 10 fits into the U-shaped edge part 6 of the cover 2. In the cavity of the reverse U-shaped edge of the lid 7 can be arranged a sealing element 11.

The lid 7 is further provided with a hand-grip 12 which bridges the edge of the lid 7. For easy handling of the hand-grip the central portion of the plate 8 is given a recessed form and support surfaces for the thumbs are arranged on the ends of the hand-grip 12.

The lid 7 likewise has a downward extending skirting 14 defining an outer peripheral wall which connects against the inside of the skirting 5 of the cover 2.

The skirting 14 of the lid 7 is provided with a number of outward extending hooks 15 which are preferably distributed regularly over the outer peripheral wall. The number of such hooks 15 is preferably at least three. The hooks 15 are each fixed resiliently to the skirting 14, for instance by arranging a substantially U-shaped recess 16 around the hook 15. The recess 16 is formed such that it extends on either side above the height of the hooks 15 so that between both "legs" of the U-shaped recess 36 a lip 17 is formed on which the hook 15 is fixed. Due to the resilience of the material the hook 15 is slightly movable in inward direction. The hook 15 is otherwise provided on the boundary of its front part and bottom part with a chamfering 18.

Arranged on the inside of the skirting 5 of the cover 2 is an edge 19 which is provided at regular distances with recesses 20 defining openings in edge 19 and wherein the width of the recesses 20 is slightly larger than the width of the hooks 15. The positions of the recesses 20 are therefore distributed along the periphery in the same manner as the hooks 15. On one side of each of the recesses 20 the edge 19 is extended downward with a piece 21.

At a distance from the other side of the recess 20 a downward extension of the edge 19 is likewise arranged in the form of a piece 21.

The embodiment described up to this point can be used for placing the lid 7 onto the cover 2. The hook 15 will herein rest on the edge 19. In this way the lid 7 can be removed again easily. It must of course be ensured during placing of the lid 7 that the hook 15 does not fall into the recess 20.

The thus obtained situation is shown in FIG. 2a and 2aa.

This embodiment offers the further possibility of using the construction as a bayonet fitting. For this purpose the hooks 15 must be moved through the recess 20, which is accompanied by a vertical movement of the lid 7, whereafter, when the level of the top side of hook 15 is located beneath the underside of edge 19, the lid 7 must be rotated to the left. This relates therefore to a horizontal movement following the vertical movement and is separate therefrom. The then obtained situation is shown in FIG. 2b and 2bb.

A chamfered cam 23 is further fixed to the skirting 5 approximately in the middle of the recess 20 at some distance below the level of the edge. The chamfered cam 23 first of all has the function of stop cam for the above outlined bayonet closure, but serves also as bearing cam for a second bayonet closure integrated under the first bayonet closure. For this purpose the lid 7 can be moved downward from the position shown in FIG. 2b, wherein the hook 15 rests against the piece 22, into a situation in which the upper side of hook 15 is located below the underside of cam 23, whereafter the situation as shown in FIG. 2c is obtained. This relates therefore to a subsequent vertical movement which is separate from the preceding horizontal movement. The lid 7 can then be rotated to the right with a separate horizontal movement. The situation as shown in FIG. 2d and 2dd is then obtained. The upper side of hook 15 herein abuts against the underside of cam 23. Particularly in this latter position it is possible to grasp the container with the handgrip 12 fixed to the lid 7. The danger that by rotating the hand-grip 12 and thus the lid 7 the latter will come loose of the cover 2 and the container is in any case small because two opposing rotation movements are necessary for this release.

Figure 2B:
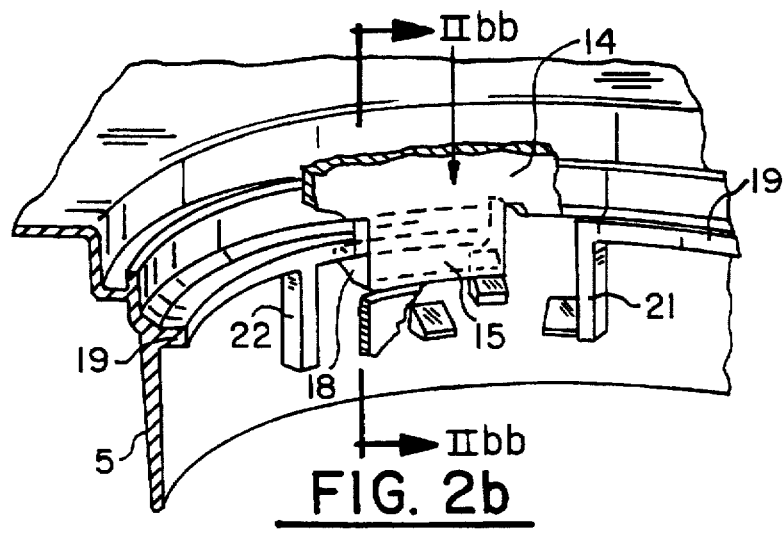
Figure 2B:
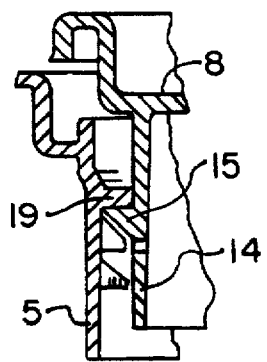
Figure 2C:
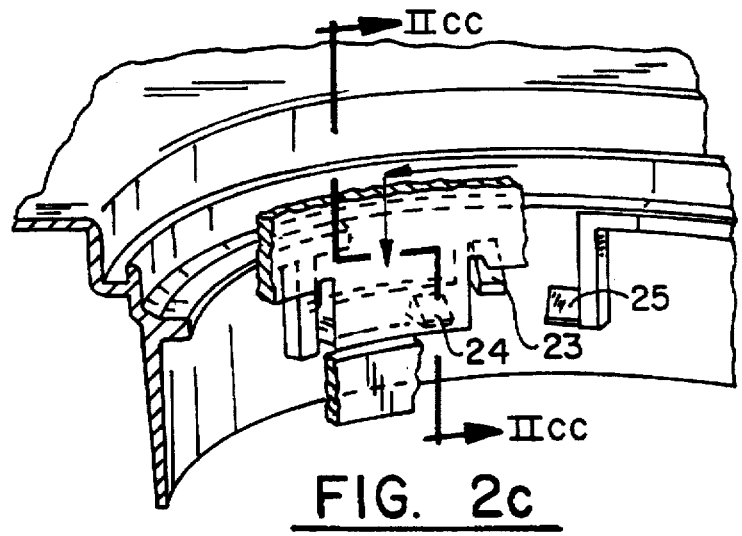
Figure 2C:
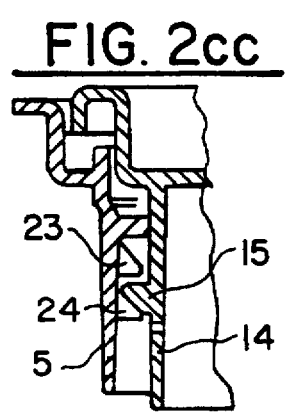
Figure 2D:
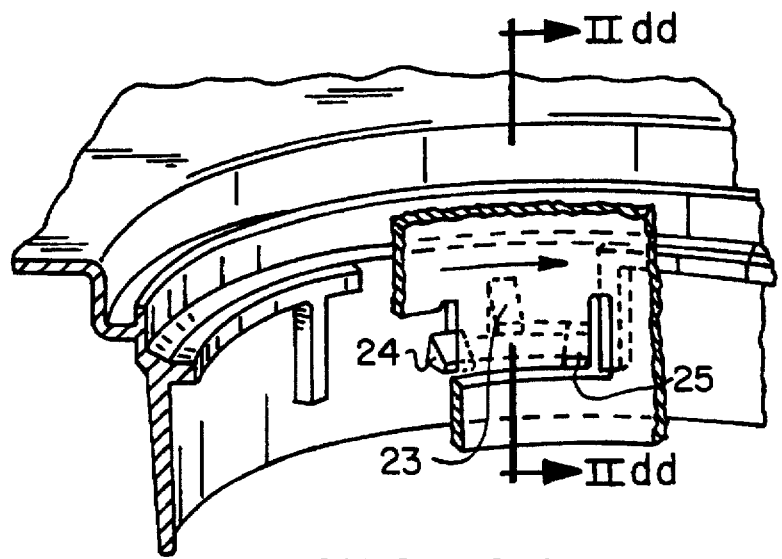
Figure 2D:
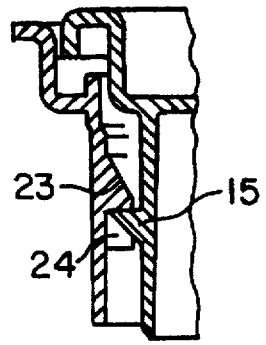

It is otherwise also possible to obtain the position shown in FIG. 2d and 2dd by pressing the lid 7 downward with force from the position shown in FIG. 2b and 2bb. The hook 15 will herein yield inwardly and move over the chamfer of cam 23 until the upper side of hook 15 engages on the underside of cam 23 and the position shown in FIG. 2d and 2dd is obtained. This relates once again to a separate vertical movement.

Finally, a pair of cams 24, 25 are arranged under the recess 20 at a level lower than the cam 23. From the position shown in FIG. 2d and 2dd it is possible to press the lid 7 downward, wherein both cams 24, 25 cause the hook 15 to move inward until the hook 15 springs back under the cams 24, 25. The lid 7 is then locked in the cover and this lid 7 can no longer be removed without destructive force.

Figure 2E:
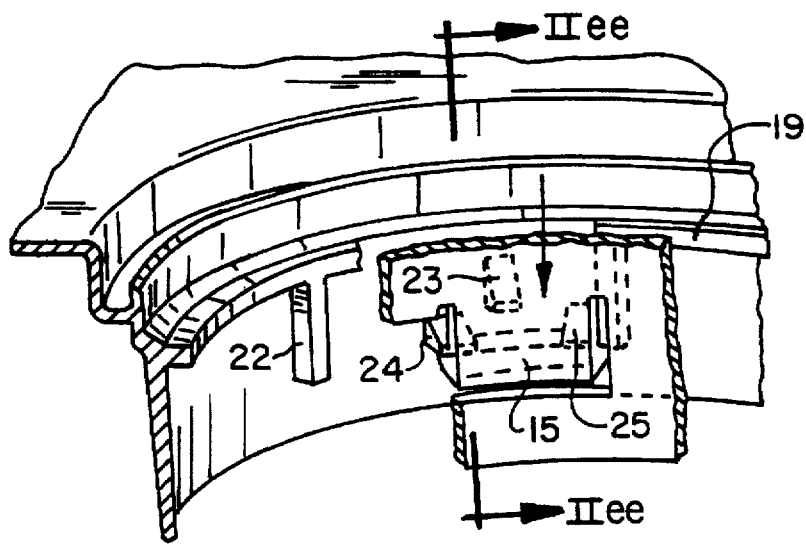
Figure 2E:
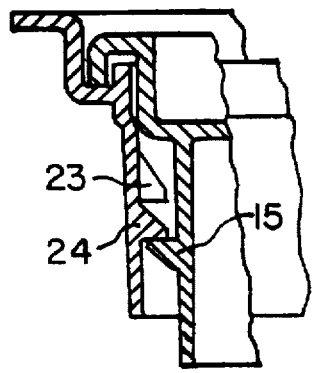
Figure 3A:
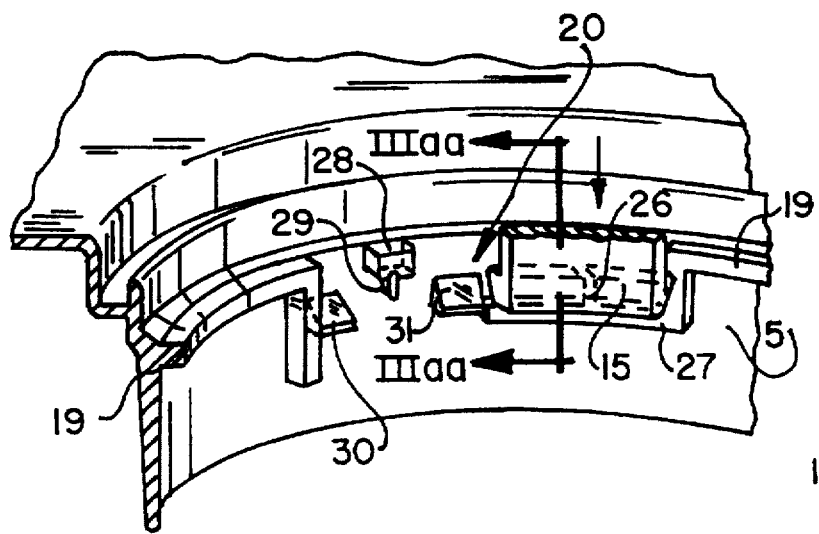
Figure 3A:
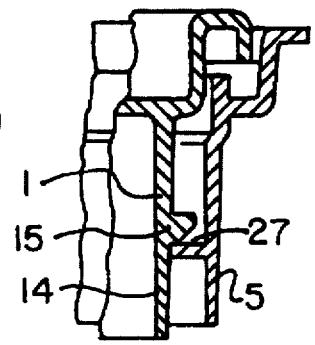
Figure 3B:
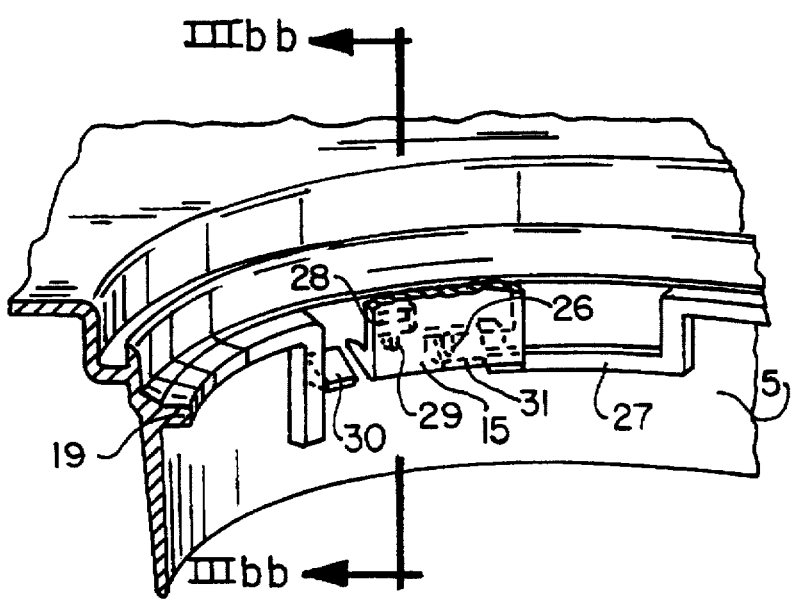
Figure 3B:
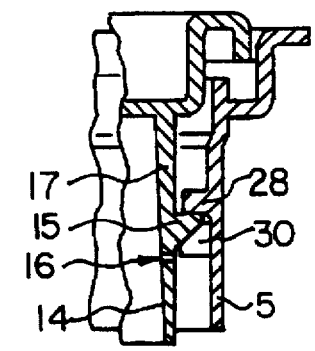

It is herein noted that it is however possible to rotate the lid 7 to the left from the then obtained position as shown in FIG. 2e and 2ee, although it is then no longer possible to move the lid 7 upward, because the distance between the extension 22 and the cam 24 is smaller than the width of the hook 15.

Shown in FIG. 3a–3d and 3aa–3dd is a second embodiment of the invention. This embodiment differs in that the openings 20 are much wider, namely, slightly more than double the width of the hook 15. A further difference in this embodiment is another configuration of the cams and the fact that a recess 26 is arranged in the hook 15. Shown in FIG. 3a and 3aa is a situation in which hook 15 is moved through the recess 20 in the edge 19 and rests on a lower-lying elongation 27 of the recess. From this situation the lid 7 can be removed easily.

As in the preceding embodiment the lid 7 can be rotated to the left, wherein the upper side of the hooks 14 abuts against the underside of a cam 28. The cam 28 is provided on its underside with a bulge 29 which fits into the recess 26 arranged in hook 15. The fitting of the bulge 29 in the recess 26 results in fixation against rotation. This situation is shown in FIG. 3c and 3cc. A horizontal movement is used for this purpose.

Further arrangedUnder the cam 28 are two cams 30, 31 which are chamfered on their upper side. From the position shown in FIG. 3c the lid 7 can be moved downward, wherein the hook 15 bends inward and moves over the inclining surfaces of the cams 30, 31 until the top side of hook 15 engages onto the underside of both said cams 30, 31. It is then no longer possible to remove the lid 7 from the cover 2. This is accompanied by a vertical movement. It will also be apparent in this embodiment that the movements of the lid 7 relative to the cover 2 in the horizontal plane and in the vertical plane take place separately.

Finally, FIG. 4a–4d and 4aa–4dd show a third embodiment. Also in this third embodiment the recess 20 is roughly equal to the width of two hooks 15. Arranged on one side of recess 20 is a pair of fingers 32, 33 which extend inclining upward and inward. As shown in FIG. 4a, the hook can be placed on these fingers. From this position the lid 7 can be easily removed.

In addition to the two fingers 32, 33 a pair of inclining cams 34, 35 are arranged on which the hook 15 can likewise be placed, whereafter the lid 7 and therewith the hooks 15 can be pressed downward with a vertical movement until the top side of hook 15 is locked beneath the undersides of cams 34, 35. This situation is shown in FIG. 4b and 4bb. From the position shown in FIG. 4b and 4bb it is possible to rotate the lid 7 to the position shown in FIG. 4c, for which only a horizontal movement is necessary, whereafter the lid 7 can be moved upward and the hooks push the fingers 32, 33 outward. It is thus possible in this manner to remove the lid 7. From both the positions shown in FIG. 4b and 4c the lid 7 can be moved downward, wherein the hook 15 bends inward against inclining surfaces of a series of lower cams 36. In the thus obtained position shown in FIG. 4d the lid 7 is fixed on the cover 2.

Figure 4:
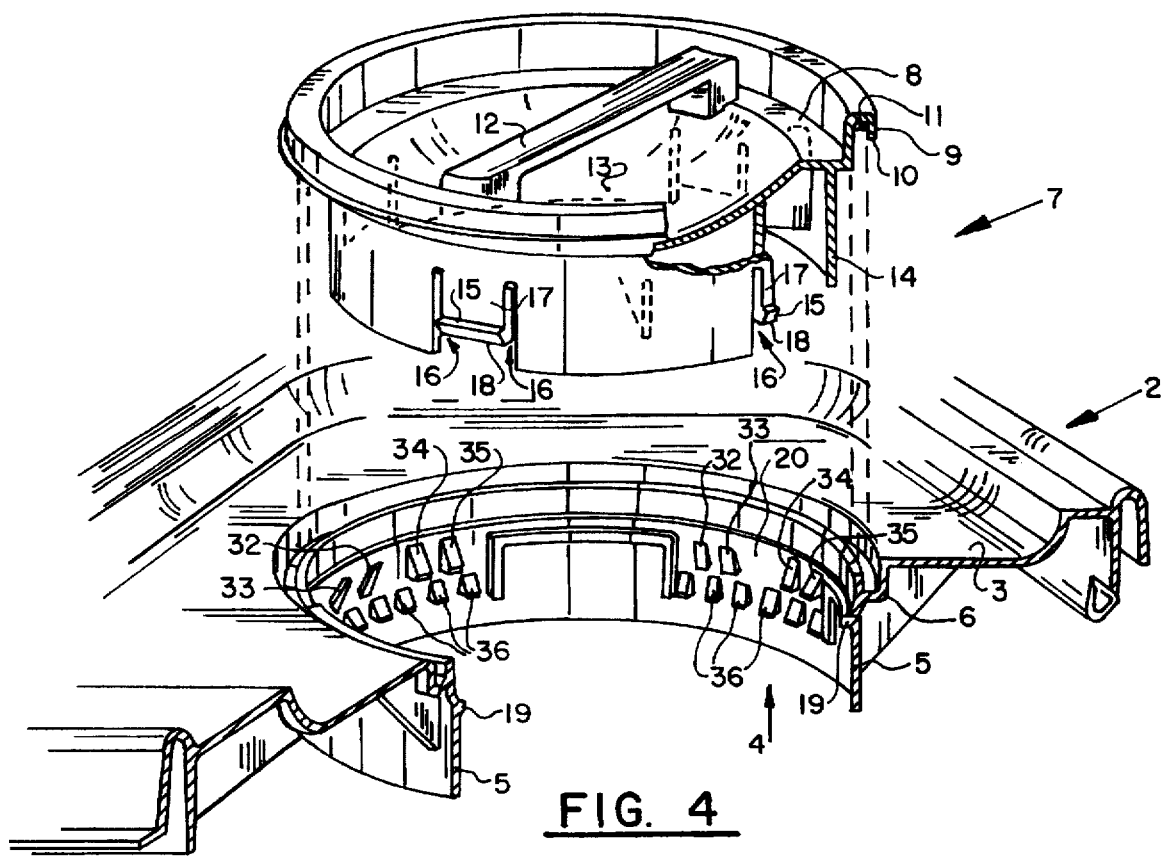
FIG. 4 shows a partly broken away view of a cover and a lid according to a third embodiment of the invention.
Figure 4C:
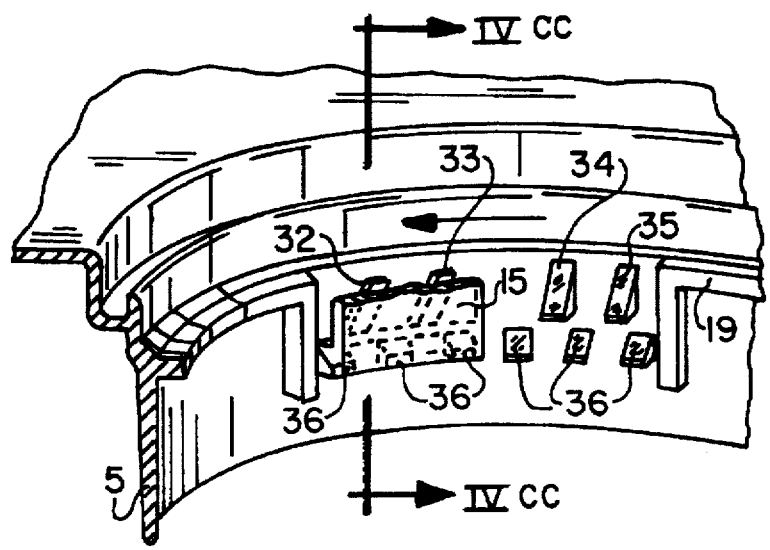
Figure 4C:
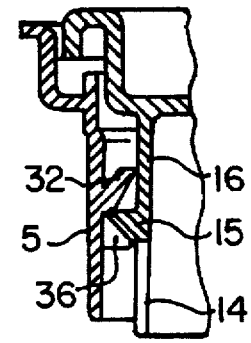
Figure 4D:
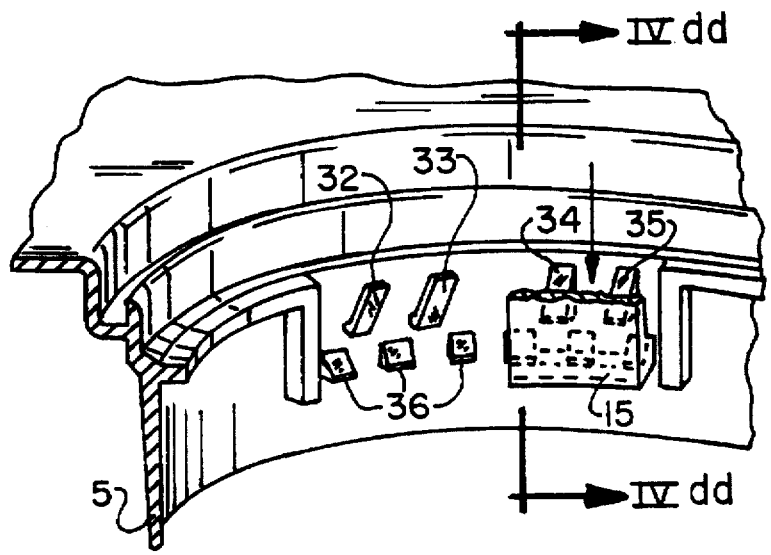
Figure 4D:
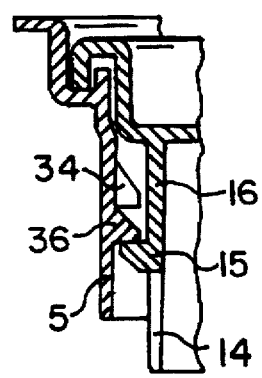
Figure 6:
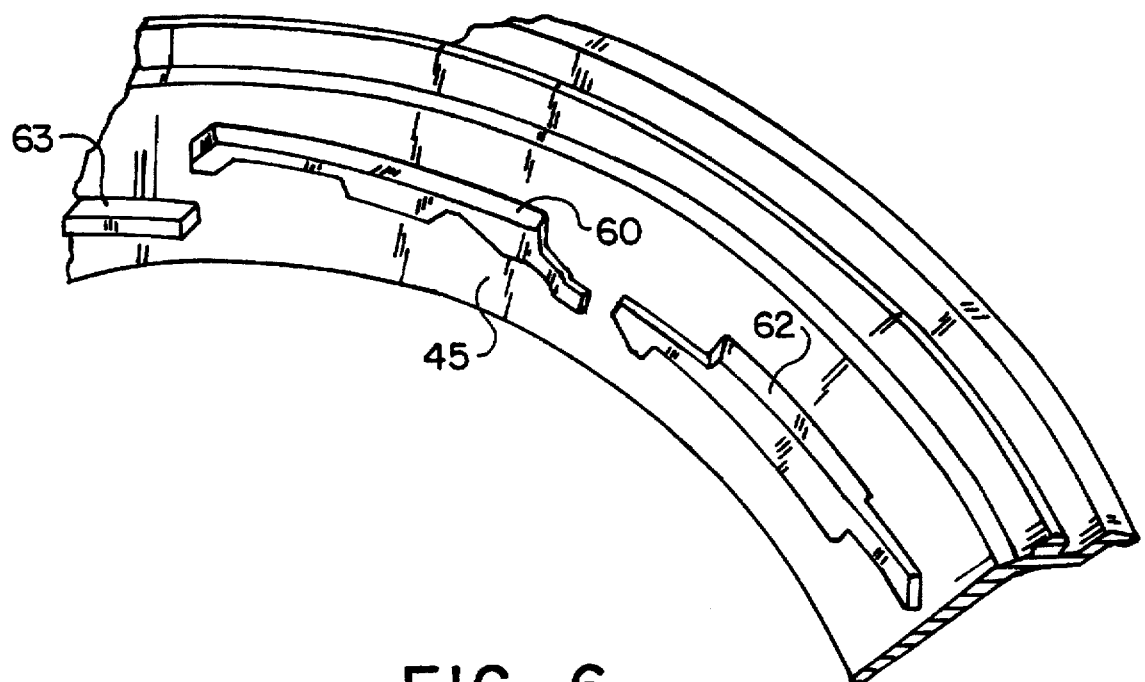
FIG. 6 shows a perspective detail of a closing cam on the cover part according to the invention.

Finally, FIG. 4 shows the total configuration of the lid 7 and the cover 2 with the associated edge and cam configuration.

Turning to the embodiment according to the FIGS. 5-7e, the closing lid 47 is substantially a cylindrical plate 48 which is provided with a standing reverse U-shaped edge 49 with downward facing outer flange 50. Flange 50 fits into the U-shaped edge part 46 of the cover 43. Placed into the cavity of the reverse U-shaped edge of the closing lid 47 is a sealing means 51.

The closing lid 47 is also provided with a hand-grip 52 which bridges the edge of the circular plate 48, and for easy handling the central portion of the lid 47 is given a recessed form at 53 and support surfaces for the thumbs are arranged on the outer ends of the hand-grip 52.

The lid 47 itself likewise has a downward oriented skirting 54 defining an outer peripheral wall which connects close-fittingly inside the downward oriented skirting 45 defining an inner periphery of the cover 43. Both skirting 45 and skirting 54 have a number of cams 60, 61 respectively which are mutually co-acting. The form and function is further elucidated hereinbelow. Further arranged on the skirting 45 of the cover 43 is a second cam 62 which lies in the line of cam 60. Finally, a third cam 63 is placed behind the cam 62 as seen in relation to cam 60.

Figure 7A:
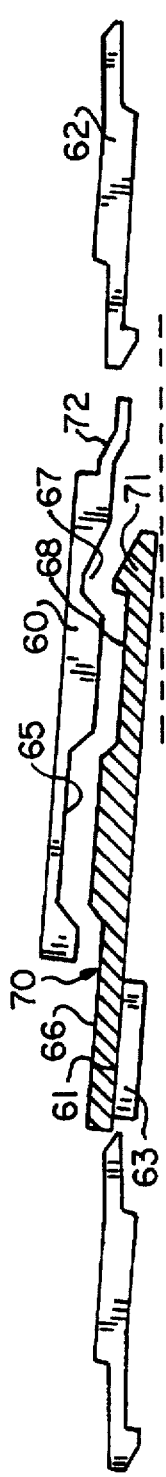
FIG. 7a–e shows a working diagram in five different positions of co-acting cams of both the lid and cover parts.
Figure 7B:
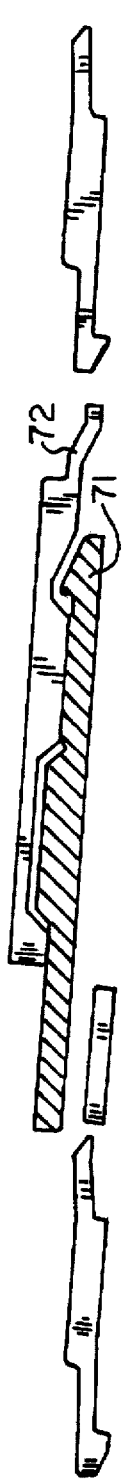

As shown in the working drawing of FIGS. 7a-7e, the cams take a substantially elongate form and are provided on the mutually facing surfaces, that is, the bottom surface of cam 60 and the top surface of cam 61, with recesses 65 respectively 66 as well as 67 and 68. The cams are moreover placed obliquely relative to the axis of the lid, which must be seen as vertical as in FIG. 2, such that the rear end of the series of cams 60, 62, 63 leaves an opening 70 relative to the front end of cam 60, which opening 70 serves as insert opening for the cam 61 of the lid 47. It is thus possible by rotating the lid 47 relative to the cover 43 to effect a sliding of the cam 61 of the lid 47 in between the respective cams 60, 63 and thus to bring about a fastening of the lid 47 in the cover 43. The position according to FIG. 7a shows the initial sliding in of the cam 61 below the cam 60. The position of FIG. 7a is obtained because the resilient portion of cam 62 springs back. When the lid 47 is not being held by the hand-grip 52 the cam 61 lies on cam 63 and thus continues to close the opening 44. In the position of FIG. 7b the lid 47 is lifted up by the hand-grip 52 and the thick portions of the cam 61 will fall into the recesses 65 and 67 of cam 60. A counter-rotation of the lid 47 relative to the cover 43 is herewith avoided and the container can be moved by hand by picking up the whole on hand-grip 52 of the closing lid 47.

Figure 7C:
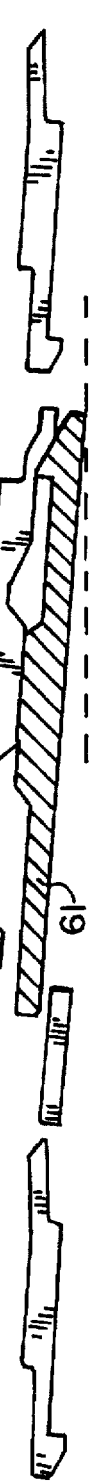

According to the position of FIG. 7c the lid can be rotated further into position for a better sealing, that is, that the sealing means 51 comes into contact with the upper end of the inner legs of U-shaped edge part 46, wherein the thickened portions of cams 60 and 61 come to lie against each other whereby vertical movement of the lid 47 relative to a cover 43 is no longer possible.

Figure 7D:

In the position as shown in FIG. 7d the lid is rotated still further in relation to the cover 43 and a hook-shaped end part 71 of cam 61 comes into contact with a resilient counter-member 72 of cam 60. Initially the resilient counter-member 72 will yield and then fall behind the hook 71 of cam 61. A counter-rotation of closing lid 47 relative to the cover 43 is hereby permanently prevented and this position should be used only when the container is wholly filled.

Figure 7E:
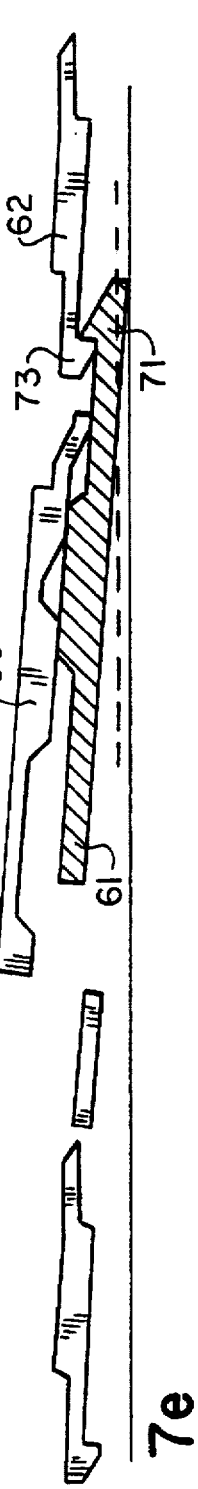

As extra safety the lid 47 can, as according to FIG. 7e, be rotated still further so that the hook-shaped end 71 of cam 61 comes to lie behind the hook-shaped end 73 of the second cam 62. This provides additional protection when for instance the seal 51 in the edge part 49 is worn out.

The invention is not limited to the above described embodiments.

We claim:

1. A cover for a waste container comprising:

a cover plate with a peripheral rim which fits onto a standing upper rim of said waste container;

said cover plate including a recessed circular opening, having an inner periphery, which is closable;

a circular lid to close said recessed circular opening of said cover plate, said lid including an outer peripheral wall which fits inside said inner periphery of said cover plate opening;

co-acting cams located on said inner periphery of said cover plate opening and said outer peripheral wall of said lid for locking said circular lid in said recessed circular opening of said cover plate; and wherein said co-acting cams on said outer peripheral wall of said lid are flexible hooks which cooperate with a plurality of said co-acting cams arranged in rows on different levels on said inner periphery of said cover plate opening.

2. A cover as claimed in claim 1, wherein said cover plate opening includes an edge extending from said inner periphery having at least one cam receiving opening to receive said co-acting cams located on said outer peripheral wall of said lid.

3. A cover as claimed in claim 2, wherein said edge includes extensions bordering at least one said cam receiving opening.

4. A cover as claimed in claim 3, wherein said edge is offset with a parallel elongation.

5. A cover for a waste container comprising:

a cover plate with a peripheral rim which fits onto a standing upper rim of said waste container;

said cover plate includinq a recessed circular opening, having an inner periphery, which is closable;

a circular lid to close said cover plate opening including an outer peripheral wall which fits inside said inner periphery of said cover plate opening;

co-acting cams located on said inner periphery of said cover plate opening and said outer peripheral wall of said lid for locking said circular lid in said cover plate opening; and wherein said co-acting cams located on said inner periphery of said cover plate opening are elongated and are disposed sloping relative to the line of symmetry of said circular lid and wherein at least one cam receiving opening is formed on the inner periphery of said cover plate opening between an end of one said co-acting cam and an other end of an adjacent one of said co-acting cams, wherein each said cam receiving opening serves for passage of one of said co-acting cams located on said outer peripheral wall of said lid, and wherein an axially oriented lower surface of at least one of said co-acting cams which are located on said inner periphery of said cover plate opening and an opposite axial surface of said co-acting cams which are located on said outer peripheral wall each have a plurality of indentations that define different closing positions of said circular lid in said cover plate.

6. A cover as claimed in claim 5, wherein a first end of said co-acting cams include a hook-shaped member and a second end of said co-acting cams include a resilient counter-member for permanent hooking of said co-acting cams into one another.

7. A cover as claimed in claim 6, further including a second cam with a hook-shaped counter-member arranged in a line of said co-acting cams.

8. A cover as claimed in claim 7, wherein said second cam includes a resilient upward oriented lip on an end remote from said counter-member.

9. A cover as claimed in claim 6, wherein said axially oriented lower surface and said opposite axial surface of said co-acting cams each include two recesses.

10. A cover as claimed in claim 5, further including a second cam with a hook-shaped counter-member arranged in a line of said co-acting cams.

11. A cover as claimed in claim 10, wherein said second cam includes a resilient upward oriented lip on an end remote from said counter-member.

12. A cover as claimed in claim 11, wherein said axially oriented lower surface and said opposite axial surface of said co-acting cams each include two recesses.

13. A cover as claimed in claim 10, wherein said axially oriented lower surface and said opposite axial surface of said co-acting cams each include two recesses.

14. A cover as claimed in claim 5, wherein said axially oriented lower surface and said opposite axial surface of said co-acting cams each include two recesses.

15. A cover for a waste container comprising:

a cover plate with a peripheral rim which fits onto a standing upper rim of said waste container;

said cover plate including a recessed circular opening, having an inner periphery, which is closable;

a circular lid to close said recessed circular opening of said cover plate, said lid including an outer peripheral wall which fits inside said inner periphery of said cover plate opening; and co-acting cams located on said inner periphery of said cover plate opening and said outer peripheral wall of said lid for locking said circular lid in a plurality of different closing positions, wherein in a first of said different closing positions said collecting cams cooperate to releasably secure said circular lid onto said cover plate, and in at least a second of said different closing positions said co-acting cams cooperate to permanently attach said circular lid to said cover plate, said co-acting cams located on said outer peripheral wall of said lid are resilient hooks which flex independent of said outer peripheral wall of said lid in a direction away from said co-acting cams located on said inner periphery of said cover plate in order to engage said co-acting cams of said inner periphery of said cover plate, and said co-acting cams located on said inner periphery of said cover plate are positioned on different levels from each other in order to define said different closing positions as said hooks engage said co-acting cams located on said inner periphery of said cover plate.

* * * * *

UNITED STATES PATENT AND TRADEMARK OFFICE
CERTIFICATE OF CORRECTION

PATENT NO.  : 5,634,566
DATED       : June 3, 1997
INVENTOR(S) : Cornelis J. Jansen, Stephanus F. Schilthuizen It is certified that error appears in the above-indentified patent and that said Letters Patent is hereby corrected as shown below:

Column 2 Line 37 "FIG." should read --FIGS.--.

Column 2 Line 42 "FIGS." should read --FIG.--.

Column 2 Line 47 "container i" should read --container 1--.

Column 2 Line 48 "container i" should read --container 1--.

Column 3 Line 12 "recess 36" should read --recess 16--.

Column 4 Line 39 "arrangedUnder" should read --arranged under--.

Signed and Sealed this

Seventh Day of October, 1997

Attest:

BRUCE LEHMAN

Attesting Officer

Commissioner of Patents and Trademarks